United States Patent [19]
Smith et al.

[11] Patent Number: 5,147,261
[45] Date of Patent: Sep. 15, 1992

[54] LIFTING BELT

[75] Inventors: Neil Smith; Gerson M. Greenbarg, both of Boca Raton, Fla.

[73] Assignee: Florida Orthopedics, Inc., Opa Locka, Fla.

[21] Appl. No.: 666,267

[22] Filed: Mar. 6, 1991

[51] Int. Cl.⁵ .......................................... A63B 21/072
[52] U.S. Cl. ...................................... 482/106; 2/338; 602/19
[58] Field of Search ................. 272/123, 143; 128/68, 128/69, 78, 87 R, 876; 2/320–338; 482/106, 108, 139; 602/19

[56] References Cited

U.S. PATENT DOCUMENTS

| | | | |
|---|---|---|---|
| 3,052,236 | 9/1962 | Schrieber | 128/78 |
| 3,097,640 | 7/1963 | Morgan | 128/78 |
| 3,970,079 | 7/1976 | Gaylord, Jr. | 128/78 |
| 4,348,774 | 9/1982 | Woodson | 2/338 |
| 4,475,543 | 10/1984 | Brooks et al. | 128/78 |
| 4,527,289 | 7/1985 | Shea | 2/322 |
| 4,545,370 | 10/1985 | Welsh | 128/78 |
| 4,552,135 | 11/1985 | Racz et al. | 128/78 |
| 4,572,167 | 2/1986 | Brodswick | 128/78 |
| 4,685,678 | 8/1987 | Newlin, Jr. | 272/123 |
| 4,689,833 | 9/1987 | Daniels | 2/322 |
| 4,745,911 | 5/1988 | Bender | 272/123 X |
| 4,768,499 | 9/1988 | Kemp | 128/78 |
| 4,782,535 | 11/1988 | Yewer, Jr. et al. | 2/321 |
| 4,802,667 | 2/1989 | Altner | 272/123 |
| 4,836,194 | 6/1989 | Sebastian et al. | 128/78 |
| 4,905,993 | 3/1990 | Barone | 272/123 |
| 4,907,576 | 3/1990 | Curlee | 128/78 |
| 4,964,401 | 10/1990 | Taigen | 272/123 X |
| 4,968,027 | 11/1990 | Anderson | 272/123 |

Primary Examiner—Robert Bahr
Attorney, Agent, or Firm—Jack E. Dominik

[57] ABSTRACT

A lifting belt which really is two belts; a lumbar belt, and an abdominal belt are enclosed. The lumbar belt is the inner belt and has a lumbar compression pad in its mid-rear portion for engaging the fifth lumbar area of the back. The two bodies extending therefrom are of a flexible material generally known as "Spandex". Metal stays are provided vertically adjacent the lumbar compression pad and vertically of the users. Releasable attachment is provided at the two end portions of the lumbar belt, one part being the loop-like material, and the other end having the hook-like material. The end with the hook-like material has loop-like material on its reverse portion. The abdominal belt is secured to the lumbar belt adjacent the lumbar compression pad and desirably has a pair of body portions which extend to their respective ends, and at the ends one has the hook-like releasable attachment member on the inner side, and the loop-like on the outer member. The remote belt end has only the hook-like member on its inside which permits it to overlappingly engage the other end which, in turn, engages the lumbar belt. The method of the invention contemplates the steps of positioning a belt as described on the lifter's body by first engaging the lumbar compression pad in the lower fifth lumbar region, and thereafter securing the lumbar belt at its releasably secured ends. The belt is worn in this fashion with the abdominal band loosely secured to the underlying lumbar belt. At the time of heavy lifting, the user stretches the abdominal belt and overlappingly secures the same firstly to the lumbar belt and thereafter to itself to firmly engage the abdominal muscles and anchor the lumbar compression pad in the lower fifth lumbar region of the back.

1 Claim, 5 Drawing Sheets

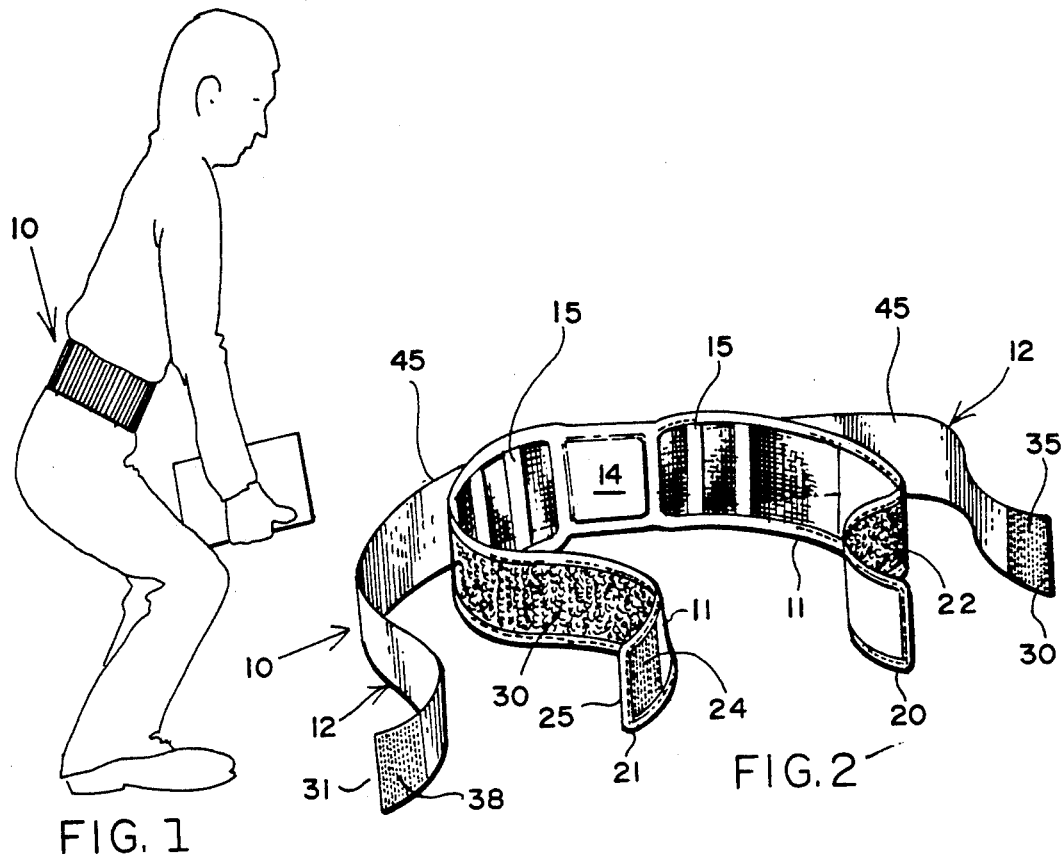
FIG. 1
FIG. 2
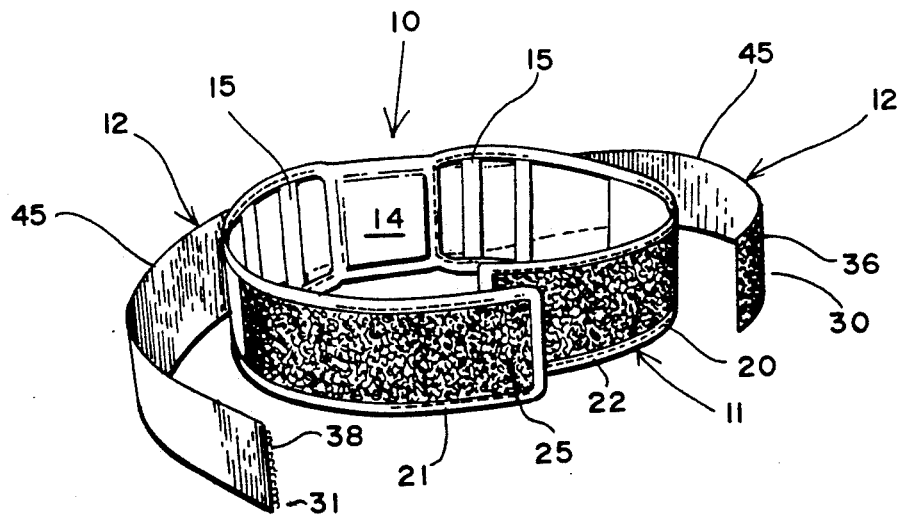
FIG. 3

LIFTING BELT

FIELD OF THE INVENTION

The present invention relates to lifting belts. These are belts generally worn by persons who perform the physical work of lifting various types of weights, whether for sport, body building, warehouse or factory. The purpose of the belts is to help reduce back injury and abdominal straining.

SUMMARY OF THE PRIOR ART

The prior art abounds. Many lifting belts are leather straps anywhere from four to eight inches wide with varying configurations, and varying techniques for securing the same in place. Some use traditional buckles, and others have begun to use VELCRO, a releasably securable pair of opposed elements.

Some of the problems of the prior art occur because they use shoulder straps. Some are the subject of complaints because they are too wide. Others are subject to complaint because they do not stretch to conform to the body. As always, there is a question of effectiveness which addresses the abdominal support and lumbar support while the user is not lifting. For example, in a warehouse the warehouse man may be driving a fork lift truck, and then have to get off of the fork lift truck and lift various boxes to put them on the shelf. If his belt is the same tightness all the time, there can be a self induced lethargic state in the abdominal and back muscles as they accommodate themselves to the tightness of the belt, and then when the flexing of the abdominal muscles is most important, they will not respond to the degree they would if the belt was adjusted just before lifting.

SUMMARY OF THE INVENTION

The present invention is directed to a lifting belt which really is two belts; a lumbar belt, and an abdominal belt. The lumbar belt is the inner belt and has a lumbar compression pad in its mid-rear portion for engaging the fifth lumbar area of the back. The two body, members extending therefrom are of Spandex, a flexible belt-like material. Metal stays are provided vertically adjacent the lumbar compression pad and vertically of the wearer. Releasable attachment is provided at the two end portions of the lumbar belt, one part being the loop-like material, and the other end having the hook-like material. The end with the hook-like material has loop-like material on its reverse portion. The abdominal belt is secured to the lumbar belt adjacent the lumbar compression pad and desirably has a pair of body portions which extend to their respective ends, and at the ends one has the hook-like releasable attachment member on the inner side, and the loop-like on the outer member. The remote belt end has only the hook-like member on its inside which permits it to overlappingly engage the other end which, in turn, engages the lumbar belt. The method of the invention contemplates the steps of positioning a belt as described on the lifter's body by first engaging the lumbar compression pad in the lower fifth lumbar region, and thereafter securing the lumbar belt at its releasably secured ends. The belt is worn in this fashion with the abdominal band loosely secured to the underlying lumbar belt. At the time of lifting, the user stretches the abdominal belt and overlappingly secures the same firstly to the lumbar belt and thereafter to itself to firmly engage the abdominal muscles and anchor the lumbar compression pad in the lower fifth lumbar region of the back.

It is a principal object of the present invention, in view of the above, to provide a lifting belt which has independent and interdependent lumbar belt portions and abdominal belt portions, and anchored to the lower back with a lumbar compression pad.

A further object of the present invention is to provide a belt with lumbar and abdominal support which is releasably secured at its end portions, and in which the abdominal outer belt is anchored to the inner lumbar belt, as well as adjustably anchored to itself to provide firm adjustable support to the wearer.

Yet another object of the present invention is to provide a belt as described which is easily adjustable within limits to varying body sizes and types, and yet readily secured.

Most importantly, a further object of the present invention looks to the provision of such a lifting belt which is high quality and yet relatively inexpensive to manufacture and bring to the market place.

BRIEF DESCRIPTION OF THE DRAWINGS

The foregoing objects and advantages will be better understood as the following description proceeds, taken in conjunction with the accompanying illustrative drawings, in which:

FIG. 1 is a side view of a man wearing a lifting belt exemplary of the present invention and lifting a load;

FIG. 2 is an exploded perspective view of the subject belt opened up to show the lumbar belt portion and the abdominal belt portion;

FIG. 3 is a view sequential to that of FIG. 2 showing the subject lifting belt being closed firstly by closing the lumbar belt;

DESCRIPTION OF PREFERRED EMBODIMENTS

Figure 4:
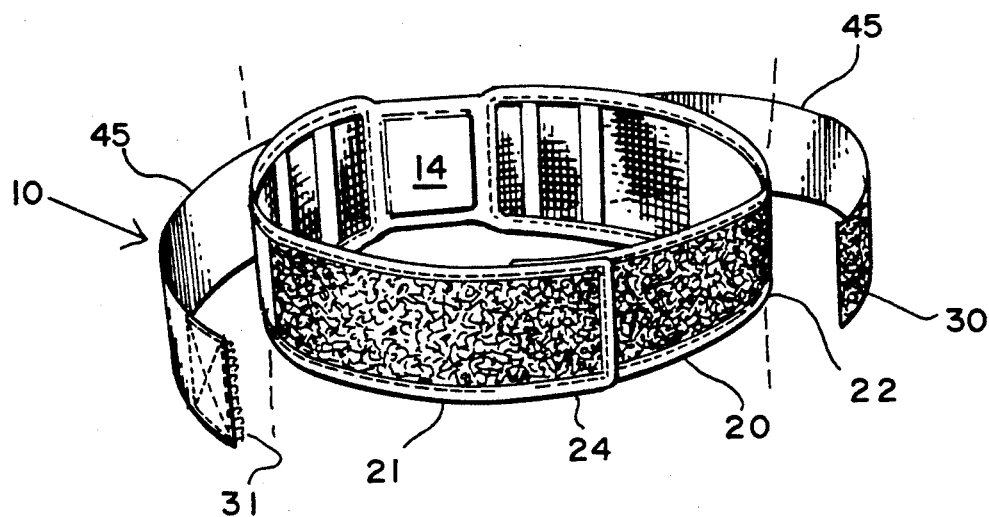
FIG. 4 is a view sequential to that of FIG. 3 showing the lumbar belt totally closed, and the abdominal belts coming toward the center.

In the illustrative drawings FIG. 1 shows a man wearing the subject lifting belt 10 in the process of lifting a weight. This weight could be a gymnastic weight, a box being lifted for storage in a warehouse, or a concrete block being lifted for use at a building sight. Numerous other types of lifting are well known, and the present invention is in anticipation of all such lifting by a human in which the back muscles, the back, and the abdominal muscles are strained in addition to the arms, shoulders, and legs.

In FIG. 2 there will be seen the illustrative lifting belt 10, which has its component parts shown as a lumbar belt 11 which is the inner belt, and which extends in two sections from a lumbar compression pad 14. A plurality of stays 15, usually four in number are provided with two on each side of the compression pad 14. The body of the lumbar belt is provided with an expandable-type material in which the stays 15 are embedded, but at its remote end portions the material is less flexible. The lumbar belt 11 relies primarily on removable and adjustable fasteners at its end to secure its adjustability, and is firmly secured to the body of the wearer. The ends of the lumbar belt 11 are a releasable inner end 20, and a releasable outer end 21. These are provided with respectively loop-type sides, and hook-type sides to releasably lock the two ends to themselves. The loop-hook relationship shown is desirable, but reversal may be used along with equivalent removable securing members.

Turning now to FIG. 3, it will be seen that there are two stages or conditions of the illustrative lifting belt 10. In the first stage the two remote ends 20, 21 of the lumbar belt portion 11 are closed, followed by the loose securement of the inner abdominal belt tab 30 to the outer portion 21 of the lumbar belt 11 and the remote portion of the abdominal belt also secured to the lumbar belt. The second or lifting stage requires the user to firmly secure the abdominal belt 12 to the lumbar belt 11 and overlappingly to itself. Specifically, the lumbar belt is shown as having three releasably secured elements 22, 24, 25. These elements contemplate remote inner end loops, remote outer end inner hooks, and remote outer end outer loops. Finally, the abdominal belt 12 has a remote inner end 30 and a remote outer end 31. The remote inner end 30 is provided with hooks 35 at its inner portion 30, and loops 36 at its outer portion. Finally, the remote outer end 31 of the abdominal belt 12 has remote end hooks 38 at its inner portion. At the other end 30, the outer loop-like elements 36 are provided to lockingly engage the opposite portion of the abdominal belt.

Figure 5:
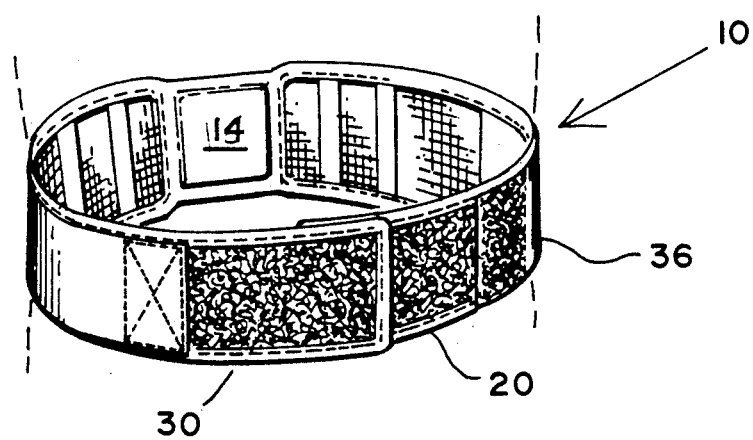
FIG. 5 is a view sequential to that of FIG. 4 showing the abdominal belt secured, but in the loose nonlifting mode.
Figure 6:
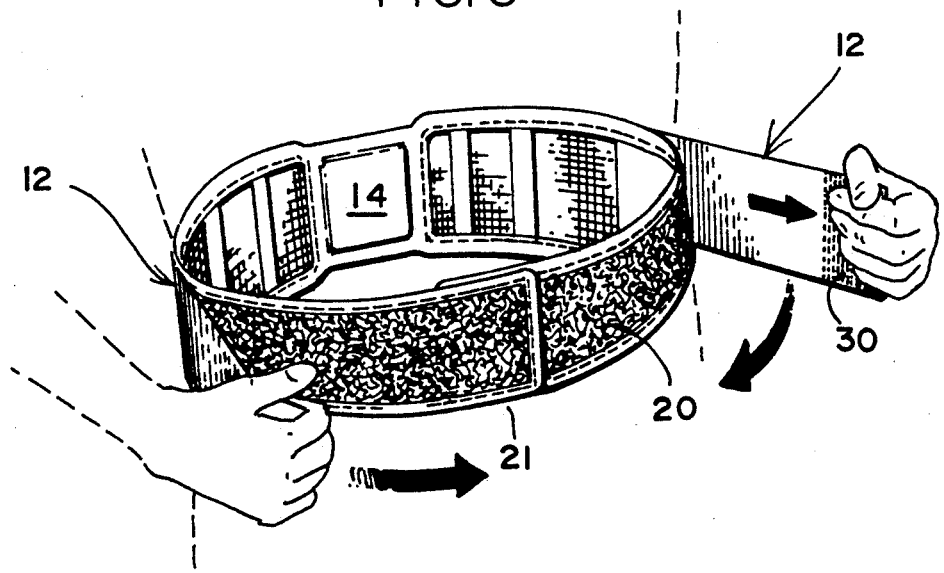
FIG. 6 is a view sequential to that of FIG. 5, showing the user preparing to readjust the abdominal belt prior to lifting.

Illustrating this sequence further, we turn now to FIG. 4. There it will be seen that the loop-like portion 22 of the inner portion 20 of the lumbar belt 11 has been engaged by the outer inner hook portion 24 of the other end 21 of the lumbar belt 11. At this stage the abdominal belt 12 has its ends 20, 21 loose. Thereafter, the user moves the abdominal belt portions to the configuration as shown in FIG. 5, whereupon the weight belt 10 is firmly secured to the body of the wearer, but not in a configuration where the abdominal muscles and the back are supported. The reason for this as set forth above is to prevent a self-induced lethargic state in the abdominal and back muscles based upon continual wear. Conversely, means are provided to further engage, and quickly, the abdominal belt 12 to the lumbar belt 11, as shown in the early stages in FIG. 6 where the wearer grasps the two ends 30, 31 of the abdominal belt 12 and holds them in a position where they can be stretched, while the lumbar belt 11 remains secured.

Figure 7:
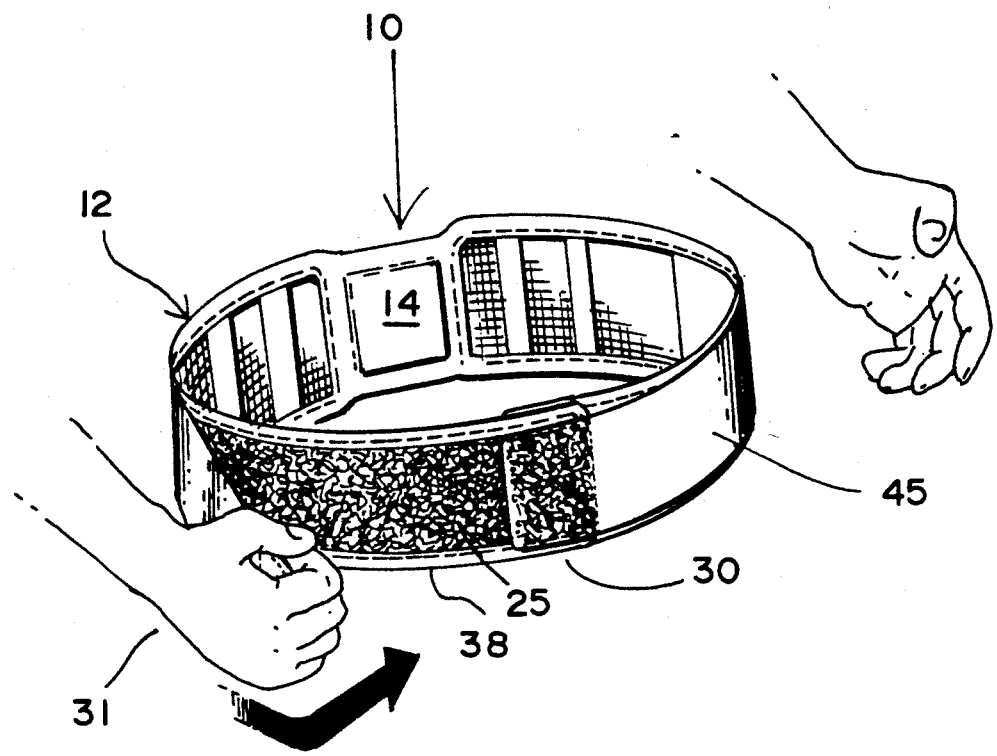
FIG. 7 is a view showing the final tab of the abdominal belt being brought to secure itself to the other end of the abdominal belt, with the abdominal belt already secured at one end to the lumbar belt.

Thereafter, as shown in FIG. 7, the first remote end 30 of the abdominal belt 12 is secured over the loop portion 25 on the outer end 21 of the lumbar belt 11. In the process, the expandable body 45 is expanded to firmly engage the abdominal muscles.

Figure 8:
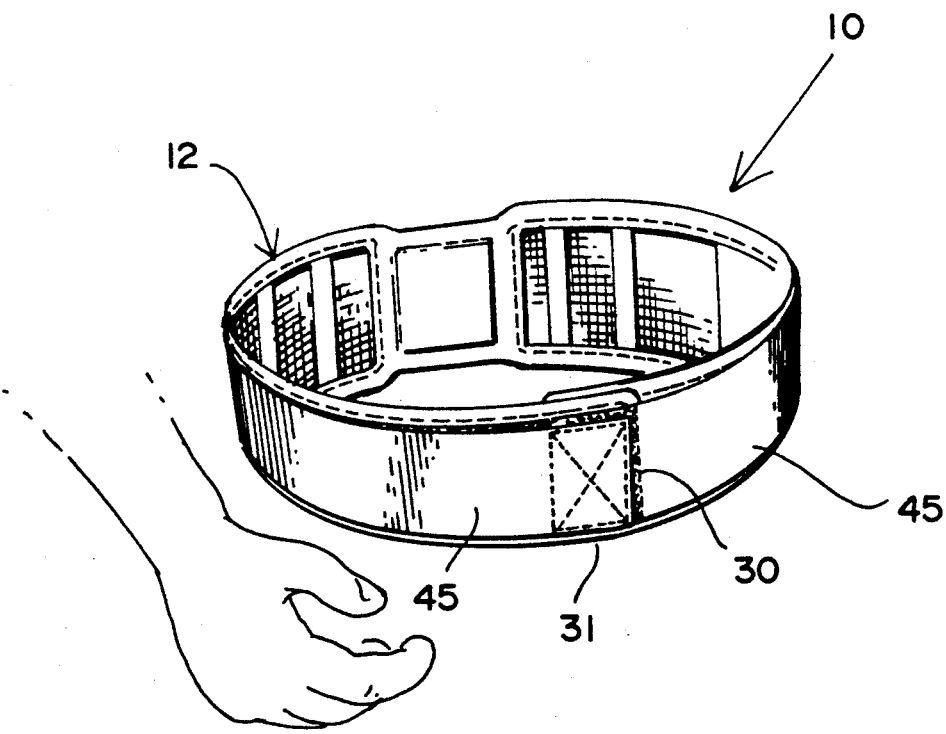
FIG. 8 is a view sequential to that of FIG. 7 showing the final securement of the last end of the abdominal belt.

Subsequently the belt is readied for the lifting, by fastening the inner hook members 38 of the outer end 31 of the abdominal belt 12 on top of the loop member 36 which is on the inner end 36 of the abdominal belt 12. Thereafter as shown in FIG. 8, the belt is ready for use and the lifter has the same in position firmly securing the compression pad to the lower fifth lumbar region of the back, and firmly securing and activating the abdominal muscles to enhance supporting strength for both the abdomen and the back.

Figure 9:
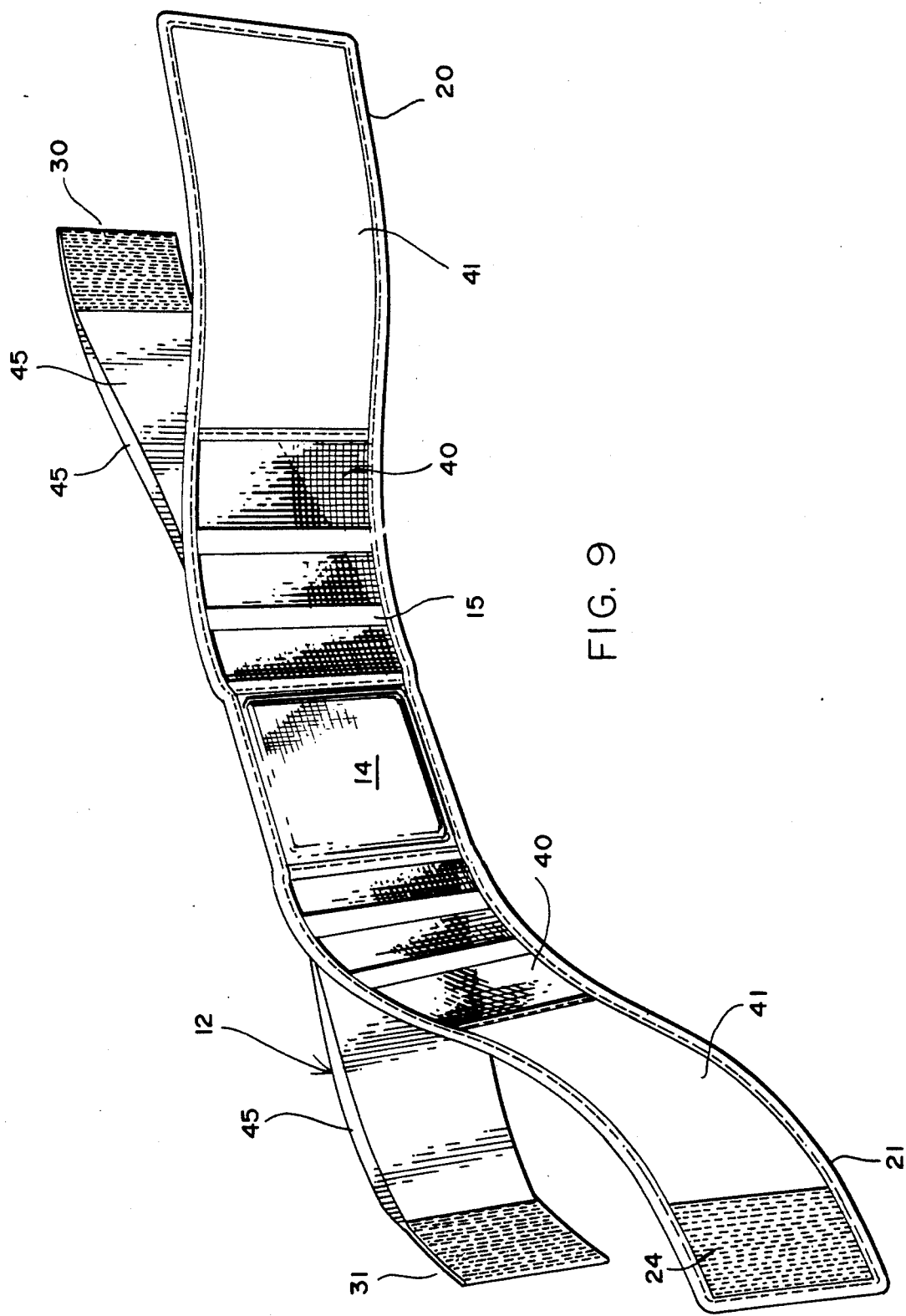
FIG. 9 is an enlarged perspective view of the subject weight belt showing its basic elements.

More specifically, the lifting belt 10 is shown enlarged in FIG. 9 where it will be seen that the lumbar belt 11 and the lumbar compression pad 14 have a relatively small expandable section 40 and relatively inflexible remote end portions 41. The stays 15 are buried in the expandable material 40 and are preferably formed of a spring steel. The inner and outer bands 45 of the abdominal belt 12 are best shown here in FIG. 9. It will be appreciated that these inner and outer sections unitize when the abdominal belt 12 is secured to the lumbar belt 11 in a configuration for lifting.

Figure 10:
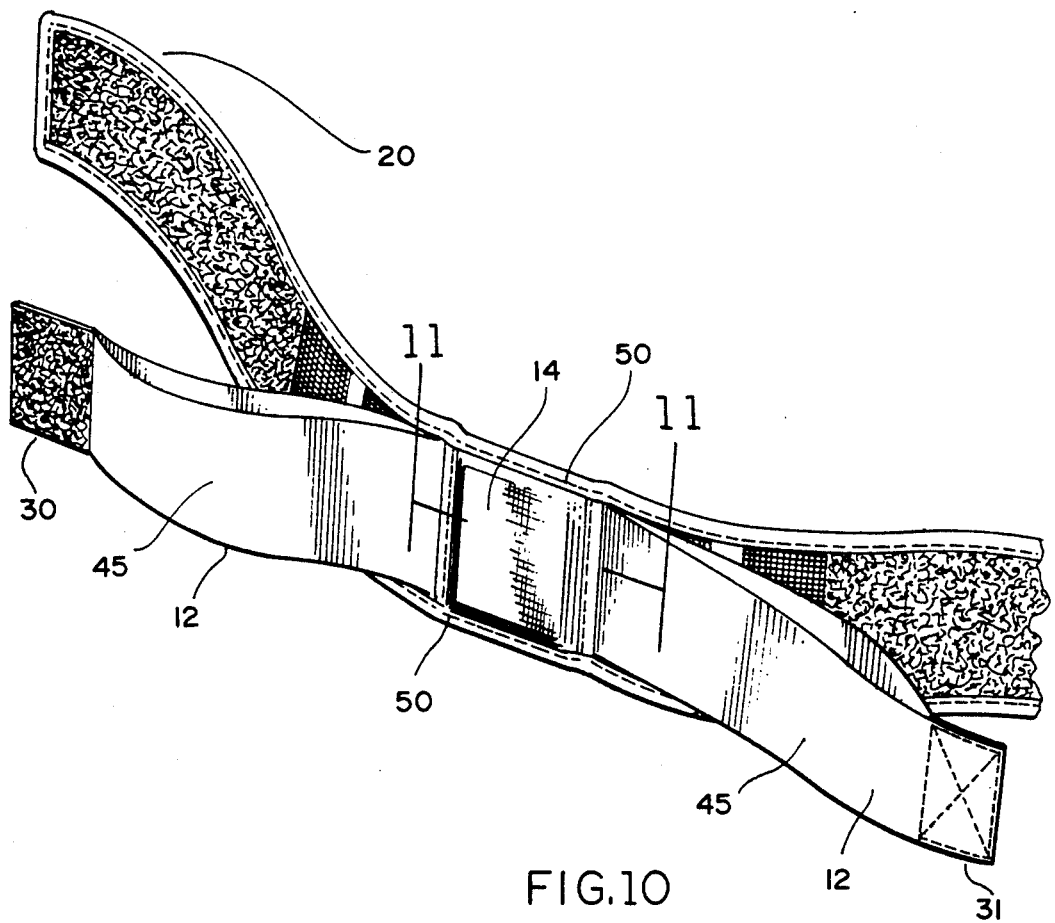
FIG. 10 is a broken view of the subject weight belt enlarged at the lumbar compression pad portion showing the relationship between the anchoring of the lumbar belt and the abdominal belt to the lumbar compression pad section.
Figure 11:
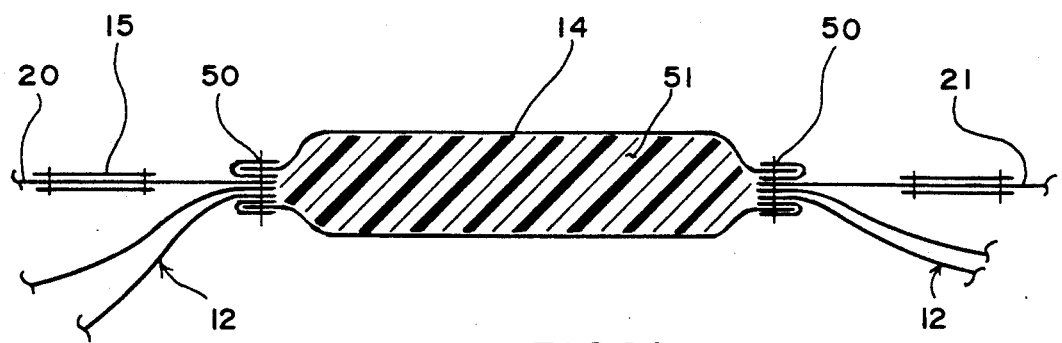
FIG. 11 is a transverse sectional view of the compression pad taken through section line 11—11 of FIG. 10.

More specifically, FIGS. 10 and 11 illustrate the securement of both the lumbar belt 11 and the abdominal belt 12 to the compression pad 14 and forming a unitary anchor portion 50. As shown in FIG. 11, the compression pad body 51 is desirably a foam polyurethane, or foamed polyethylene, having a firm configuration and body makeup, but sufficiently flexible to bend to conform to vertebrae so that there will not be a rubbing or strong compressive effect immediately against the vertebrae in the lumbar portion of the back which the compression pad overlies.

Although particular embodiments of the invention have been shown and described in full here, there is no intention to thereby limit the invention to the details of such embodiments. On the contrary, the intention is to cover all modifications, alternatives, embodiments, usages and equivalents as fall within the spirit and scope of the present invention, specification and appended claims.

What is claimed is:
1. A lifting belt comprising, in combination,
a lumbar belt portion
a compression pad at a mid-portion in the rear of the lumbar belt,
said lumbar belt having two ends, each of which has releasable securable material thereon for securing the lumbar belt around the waist of a lifter with the lumbar compression pad overlying the back of the user,
an abdominal belt having two portions,
each of the portions of the abdominal belt being anchored adjacent the lumbar compression pad of the lumbar belt,
each of said abdominal belt portions having an expandable type material,
each of said abdominal belt portions having releasable secured end members,
said abdominal belt having overlapping releasable securable members at its end on both side thereof,
said abdominal belt having a first end member engageable to the releasable securing material on the outer portion of the second lumbar belt member and means on its opposite side portion of the end to engage a further releasable securable member on the lower belt member, and an inner releasable securable member on the outer end of the abdominal belts for overlapping securement to its underlying and mating releasable lumbar belt portion, whereby the lumbar belt provides the inner support to the back and the abdomen, and the adjustable outer abdominal belt may be worn loosely and thereafter secured in position to augment the support function of the combination of belts.

* * * * *